(12) United States Patent
Menn

(10) Patent No.: US 10,702,277 B2
(45) Date of Patent: Jul. 7, 2020

(54) SURGICAL CLIP FOR LAPAROSCOPIC PROCEDURES

(71) Applicant: CONMED Corporation, Utica, NY (US)

(72) Inventor: Pavel Menn, Marblehead, MA (US)

(73) Assignee: CONMED CORPORATION, Utica, NY (US)

( * ) Notice: Subject to any disclaimer, the term of this patent is extended or adjusted under 35 U.S.C. 154(b) by 354 days.

(21) Appl. No.: 15/423,893

(22) Filed: Feb. 3, 2017

(65) Prior Publication Data
US 2017/0209149 A1 Jul. 27, 2017

Related U.S. Application Data

(63) Continuation of application No. 13/045,519, filed on Mar. 10, 2011, now Pat. No. 9,597,089.
(Continued)

(51) Int. Cl.
*A61B 17/122* (2006.01)
*A61B 17/08* (2006.01)
(Continued)

(52) U.S. Cl.
CPC ........ *A61B 17/122* (2013.01); *A61B 17/1285* (2013.01); *A61B 17/08* (2013.01);
(Continued)

(58) Field of Classification Search
CPC ..... A61B 17/122; A61B 17/282; A61B 17/08; A61B 17/12; A61B 17/083; A61B 17/22;
(Continued)

(56) References Cited

U.S. PATENT DOCUMENTS 2,618,268 A * 11/1952 English ................ A61B 17/282
227/19
2,796,065 A 6/1957 Kapp
(Continued)

FOREIGN PATENT DOCUMENTS

WO WO2011/0112877 9/2011

OTHER PUBLICATIONS

Office Action for U.S. Appl. No. 13/045,519, dated Nov. 21, 2012, 9 pages.
(Continued)

*Primary Examiner* — Christopher L Templeton

(57) ABSTRACT

A surgical clip for a clip applier to ligate vessels. The clip contains two opposing legs connected in parallel by an apex to form a U-shape. Each leg has an outer surface with a half-round cross-sectional configuration for minimizing tissue damage by preventing clip scissoring during ligation. Each leg has an inner surface with a flat central surface, two concave grooves on opposing sides of the central surface, and two convex ridges on opposing sides of the each groove. As a vessel is ligated, vessel tissue moves into the concave grooves while remaining frictionally engaged by the compressive forces applied by the central surfaces and convex ridges of each leg so that the clip does not move on the vessel. The edges of the grooves and the edges of the ridges of each leg are rounded to prevent any cutting of the ligated vessel.

3 Claims, 14 Drawing Sheets

US 10,702,277 B2

Page 2

Related U.S. Application Data

(60) Provisional application No. 61/312,505, filed on Mar. 10, 2010.

(51) Int. Cl.
*A61B 17/12* (2006.01)
*A61B 17/128* (2006.01)
*A61B 17/00* (2006.01)

(52) U.S. Cl.
CPC ..... *A61B 17/12* (2013.01); *A61B 2017/00004* (2013.01); *A61B 2017/00778* (2013.01)

(58) Field of Classification Search
CPC ...... A61B 17/1227; A61B 2017/12009; A61B 2017/081; A61B 2017/0488; A61B 2017/2808; A61B 2017/2926; F16B 2/26; B65D 33/1641; B65D 33/1633; B65D 33/1616
See application file for complete search history.

(56) References Cited

U.S. PATENT DOCUMENTS

| | | | |
|---|---|---|---|
| 2,818,871 A | 1/1958 | Beaudry | |
| 3,363,628 A * | 1/1968 | Wood | A61B 17/122 206/339 |
| 3,541,647 A | 11/1970 | Marietta | |
| 3,608,554 A * | 9/1971 | McGuinness | A61B 17/282 24/518 |
| 3,867,944 A | 2/1975 | Samuels | |
| 3,874,042 A * | 4/1975 | Eddleman | A61B 17/122 251/10 |
| 3,926,195 A | 12/1975 | Bleier et al. | |
| 3,978,555 A | 9/1976 | Weisenthal | |
| 4,188,953 A | 2/1980 | Klieman et al. | |
| 4,192,313 A | 3/1980 | Ogami | |
| 4,308,641 A * | 1/1982 | Niedecker | B65D 33/1641 24/30.5 W |
| 4,693,251 A | 9/1987 | Bleier et al. | |
| 4,702,247 A | 10/1987 | Blake, III et al. | |
| 4,799,481 A | 1/1989 | Transue et al. | |
| 4,844,066 A | 7/1989 | Stein | |
| 4,976,721 A | 12/1990 | Blasnik et al. | |
| 4,976,722 A | 12/1990 | Failla | |
| 4,979,950 A | 12/1990 | Transue et al. | |
| 5,026,382 A | 6/1991 | Peiffer | |
| 5,201,746 A | 4/1993 | Shichman | |
| 5,366,458 A | 11/1994 | Korthoff et al. | |
| 5,428,871 A | 7/1995 | Iosif | |
| 5,501,693 A * | 3/1996 | Gravener | A61B 17/122 606/157 |
| 5,509,920 A | 4/1996 | Phillips et al. | |
| 5,571,121 A | 11/1996 | Heifetz | |
| 5,601,573 A | 2/1997 | Fogelberg et al. | |
| 5,620,452 A | 4/1997 | Yoon | |
| 5,626,585 A | 5/1997 | Mittelstadt et al. | |
| 5,626,586 A | 5/1997 | Pistl et al. | |
| 5,626,592 A | 5/1997 | Phillips et al. | |
| 5,643,291 A | 7/1997 | Pier et al. | |
| 5,695,502 A | 12/1997 | Pier et al. | |
| 5,713,911 A | 2/1998 | Racenet et al. | |
| 5,755,726 A | 5/1998 | Pratt et al. | |
| 5,772,673 A | 6/1998 | Cuny et al. | |
| 5,833,696 A | 11/1998 | Whitfield et al. | |
| 5,858,018 A | 1/1999 | Shipp et al. | |
| 5,895,394 A | 4/1999 | Kienzle et al. | |
| 5,904,693 A | 5/1999 | Dicesare et al. | |
| 5,938,666 A * | 8/1999 | Reynolds | A61B 17/122 606/120 |
| 5,993,465 A | 11/1999 | Shipp et al. | |
| 6,015,417 A * | 1/2000 | Reynolds, Jr. | A61B 17/064 606/151 |
| 6,059,799 A | 5/2000 | Aranyi et al. | |
| 6,210,419 B1 | 4/2001 | Mayenberger et al. | |
| 6,217,590 B1 | 4/2001 | Levinson | |
| 6,226,843 B1 | 5/2001 | Crainich | |
| 6,261,303 B1 | 7/2001 | Mayenberger et al. | |
| 6,306,149 B1 | 10/2001 | Meade | |
| 6,306,150 B1 | 10/2001 | Levinson | |
| 6,350,269 B1 | 2/2002 | Shipp et al. | |
| 6,537,289 B1 | 3/2003 | Kayan et al. | |
| 6,607,540 B1 | 8/2003 | Shipp | |
| 6,610,073 B1 | 8/2003 | Levinson | |
| 6,640,870 B2 | 11/2003 | Osinga | |
| 6,652,539 B2 | 11/2003 | Shipp et al. | |
| 6,673,083 B1 | 1/2004 | Kayan et al. | |
| 6,695,854 B1 | 2/2004 | Kayan et al. | |
| 6,793,663 B2 | 9/2004 | Kneifel et al. | |
| 6,824,547 B2 | 11/2004 | Wilson, Jr. et al. | |
| 6,837,895 B2 | 1/2005 | Mayenberger | |
| 6,869,435 B2 | 3/2005 | Blake, III | |
| 6,911,033 B2 | 6/2005 | de Guillebon et al. | |
| 7,207,997 B2 | 4/2007 | Shipp et al. | |
| 7,261,724 B2 | 8/2007 | Molitor et al. | |
| 7,297,149 B2 | 11/2007 | Vitali et al. | |
| 7,316,693 B2 | 1/2008 | Viola | |
| 7,316,696 B2 | 1/2008 | Wilson, Jr. et al. | |
| 7,326,223 B2 | 2/2008 | Wilson, Jr. | |
| D572,363 S | 7/2008 | Menn | |
| 7,431,724 B2 | 10/2008 | Manetakis et al. | |
| 7,572,266 B2 | 8/2009 | Young et al. | |
| 7,582,095 B2 | 9/2009 | Shipp et al. | |
| 7,585,304 B2 | 9/2009 | Hughett | |
| 7,594,920 B2 | 9/2009 | Kayan et al. | |
| 7,637,917 B2 | 12/2009 | Whitfield et al. | |
| 7,678,125 B2 | 3/2010 | Shipp | |
| 7,686,820 B2 | 3/2010 | Huitema et al. | |
| 7,699,860 B2 | 4/2010 | Huitema et al. | |
| 7,713,276 B2 | 5/2010 | Dennis | |
| 7,717,926 B2 | 5/2010 | Whitfield et al. | |
| 7,727,248 B2 | 6/2010 | Smith et al. | |
| 7,731,724 B2 | 6/2010 | Huitema et al. | |
| 7,819,886 B2 | 10/2010 | Whitfield et al. | |
| 7,896,869 B2 | 3/2011 | DiSilvestro et al. | |
| 7,905,890 B2 | 3/2011 | Whitfield et al. | |
| 7,942,885 B2 | 5/2011 | Sixto, Jr. et al. | |
| 8,021,375 B2 | 9/2011 | Aldrich et al. | |
| 8,038,686 B2 | 10/2011 | Huitema et al. | |
| 8,137,368 B2 | 3/2012 | Kayan et al. | |
| 8,172,870 B2 | 5/2012 | Shipp | |
| 8,236,012 B2 | 8/2012 | Molitor et al. | |
| 8,262,679 B2 | 9/2012 | Nguyen | |
| 8,267,944 B2 | 9/2012 | Sorrentino et al. | |
| 8,267,946 B2 | 9/2012 | Whitfield et al. | |
| 8,282,655 B2 | 10/2012 | Whitfield et al. | |
| 8,287,559 B2 | 10/2012 | Barker et al. | |
| 8,357,171 B2 | 1/2013 | Whitfield et al. | |
| 8,372,095 B2 | 2/2013 | Viola | |
| 8,382,773 B2 | 2/2013 | Whitfield et al. | |
| 8,409,222 B2 | 4/2013 | Whitfield et al. | |
| 8,409,223 B2 | 4/2013 | Sorrentino et al. | |
| 8,419,752 B2 | 4/2013 | Sorrentino et al. | |
| 8,465,502 B2 | 6/2013 | Zergiebel | |
| 8,486,091 B2 | 7/2013 | Sorrentino et al. | |
| 8,491,608 B2 | 7/2013 | Sorrentino et al. | |
| 8,523,882 B2 | 9/2013 | Huitema et al. | |
| 8,556,920 B2 | 10/2013 | Huitema et al. | |
| 8,579,918 B2 | 11/2013 | Whitfield et al. | |
| 8,585,717 B2 | 11/2013 | Sorrentino et al. | |
| 8,998,935 B2 | 4/2015 | Hart | |
| 9,597,089 B2 | 3/2017 | Menn | |
| 2002/0177863 A1 | 11/2002 | Mandel et al. | |
| 2004/0153107 A1 | 8/2004 | Jervis et al. | |
| 2005/0149068 A1* | 7/2005 | Williams | A61B 17/122 606/151 |
| 2005/0273122 A1 | 12/2005 | Theroux et al. | |
| 2006/0212049 A1 | 9/2006 | Mohiuddin | |
| 2006/0235468 A1 | 10/2006 | Huitema et al. | |
| 2007/0162060 A1 | 7/2007 | Wild | |
| 2007/0173866 A1 | 7/2007 | Sorrentino et al. | |
| 2008/0312670 A1* | 12/2008 | Lutze | A61B 17/122 606/157 |
| 2009/0076533 A1 | 3/2009 | Kayan et al. | |

(56) References Cited

U.S. PATENT DOCUMENTS

| | | |
|---|---|---|
| 2011/0224701 A1 | 9/2011 | Menn |
| 2011/0230900 A1 | 9/2011 | Sarradon |
| 2011/0295290 A1 | 12/2011 | Whitfield |
| 2012/0083803 A1 | 4/2012 | Patel et al. |
| 2012/0226291 A1 | 9/2012 | Malizia et al. |
| 2013/0172914 A1 | 7/2013 | Weisshaupt |
| 2013/0178880 A1 | 7/2013 | Keller |
| 2013/0184726 A1 | 7/2013 | Weisshaupt et al. |
| 2013/0245651 A1 | 9/2013 | Schmidt et al. |
| 2013/0245653 A1 | 9/2013 | Litherland |
| 2014/0171986 A1 | 6/2014 | Shelton |

OTHER PUBLICATIONS

Office Action for U.S. Appl. No. 13/045,519, dated Jul. 17, 2013, 10 pages.
Office Action for U.S. Appl. No. 13/045,519, dated Nov. 3, 2014, 8 pages.
Office Action for U.S. Appl. No. 13/045,519, dated Jul. 9, 2015, 12 pages.
Office Action for U.S. Appl. No. 13/045,519, dated Apr. 8, 2016, 16 pages.
International Search Report and Written Opinion for International Application No. PCT/US2011/028006, dated May 3, 2011.
International Preliminary Report on Patentability Chapter I for International Application No. PCT/US2011/028006, dated Sep. 11, 2012.

* cited by examiner

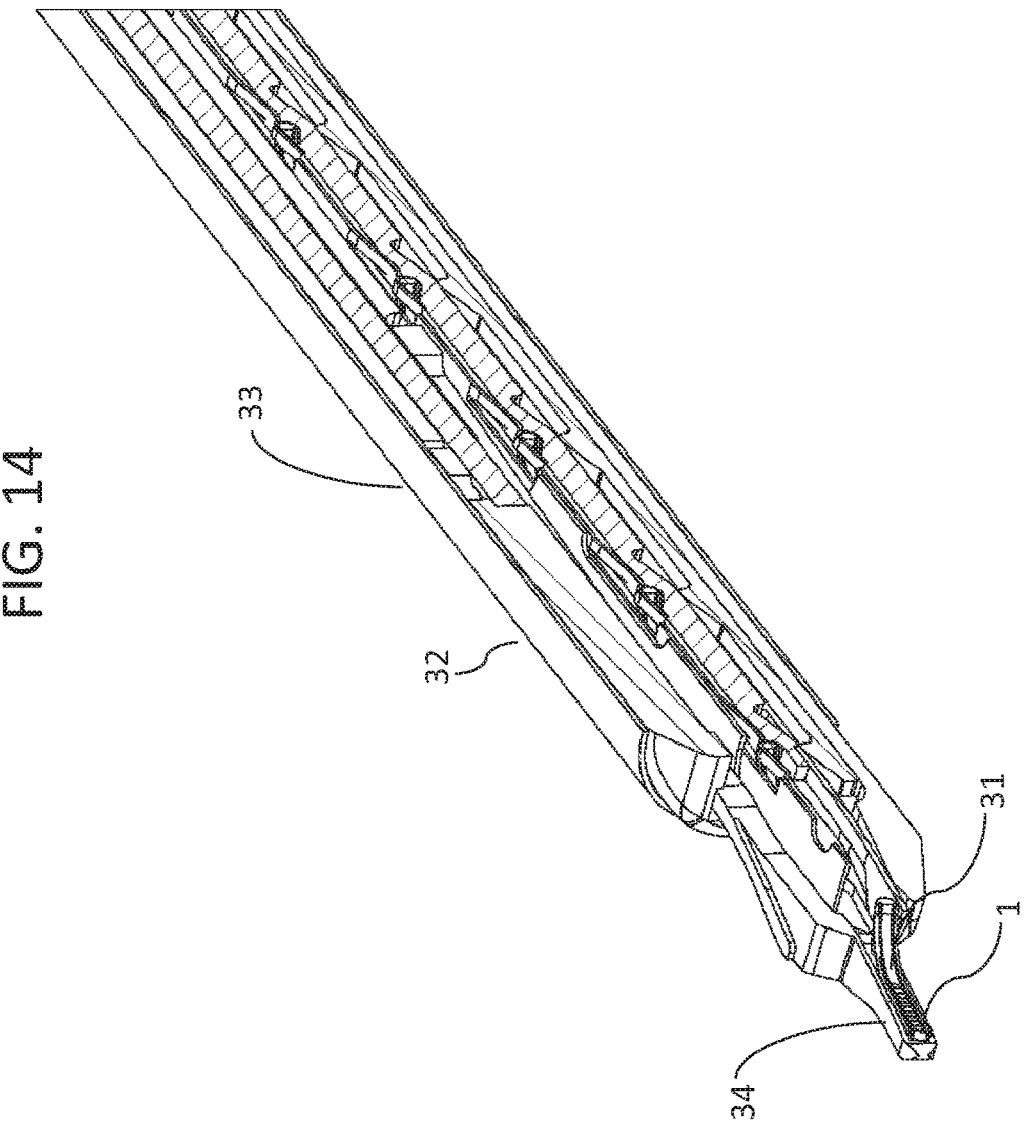

SURGICAL CLIP FOR LAPAROSCOPIC PROCEDURES

CROSS REFERENCE TO RELATED APPLICATION

This application claims the benefit of U.S. Provisional Patent Application No. 61/312,505 filed on Mar. 10, 2010, the contents of which are incorporated herein by reference.

FIELD OF THE INVENTION

This invention relates to novel surgical ligation clips for ligating blood vessels during laparoscopic or endoscopic procedures.

BACKGROUND OF INVENTION

In order to operate on a given tissue or a blood vessel, surgeons must ligate or occlude nearby blood vessels to prevent patient blood loss.

Since laparoscopic and endoscopic surgical procedures are conducted through a small incision in the skin or natural body orifices, the surgeon must have long and narrow tools to complete this ligation or occlusion of blood vessels. These tools must be small enough to be inserted through an incision and long enough to reach the desired blood vessels within the patient.

Surgeons employ small surgical clips and long clip appliers to ligate or occlude blood vessels in laparoscopic and endoscopic surgical procedures. These surgical clips need to perform multiple functions.

First, the surgical clip must be securely fastened to the blood vessel. Movement or slippage of the surgical clip on the vessel should be minimized or eliminated once the clip has been applied. Second, the surgical clip should completely close the blood vessel to which it is applied. Movement or slippage of the surgical clip or failure to fully close a blood vessel may cause one or more of the following: damage to nearby tissue, interference on the surgical site, patient blood loss, a lethal drop in blood pressure, or loss of the clip inside the patient.

Third, the surgical clip should be designed to minimize damage to the closed blood vessel and surrounding tissue as much as possible. Surgical clips that cause tissue or blood vessel damage may result in internal bleeding a lethal drop in blood pressure, infections, or longer recovery periods.

Examples of surgical clips are described in U.S. Pat. Nos. 6,610,073; 6,217,590; 5,509,920; 5,501,693; 5,201,746; 5,171,253; 5,171,252; 5,100,420; 5,084,057; 5,026,382; 4,971,198; 4,976,722; 4,979,950; 4,844,066; 4,799,481; 4,702,247; 4,414,721; 4,188,953; 4,146,130; 3,867,944; and 3,363,628; and U.S. Published Patent Application Nos. 2007/0173866; 2005/0273122; and 2004/0153107; all of which are herein incorporated by reference in their entirety.

These previously disclosed surgical clips do not adequately securely fasten to and completely close a blood vessel while minimizing surrounding tissue damage. Another problem for these previously disclosed surgical clips is the phenomenon known as the "scissoring" effect Previously disclosed surgical clips are either U-shaped or V-shaped. These shapes are defined by a pair of legs joined at a proximate end by an apex and spaced apart at a distal end to define a space between the legs. A clip applier places a surgical clip over a blood vessel within this space and compresses the legs to ligate the vessel.

Scissoring occurs when, due to deformation of the surgical clips in the clip applier, the legs do not align and are offset at the distal ends with respect to each other. This misalignment causes the surgical clip to cut or sever blood vessels during application. Scissoring can also prevent the clip from completely closing the vessel.

Accordingly, the subject invention is a novel surgical clip that securely fastens to and completely closes a blood vessel while minimizing surrounding tissue damage. In addition, this novel surgical clip prevents vessel damage due to the "scissoring" effect.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a surgical clip, comprising: A a relatively non-deformable first elongated leg member extending along a first leg axis from a first proximal end to a first distal end, and having an outer lateral surface extending along the first leg axis and an inner lateral surface extending along the first leg axis, and wherein the first elongated leg member has a substantially D-shaped cross-section transverse to the first leg axis and defined by a curved boundary component in the outer lateral surface, and a substantially straight boundary component in the inner lateral surface, B. a relatively non-deformable second elongated leg member extending along a second leg axis from a second proximal end to a second distal end, and having an inner lateral surface extending along the second leg axis and an outer lateral surface extending along the second leg axis, and wherein the second elongated leg member has a substantially D-shaped cross-section transverse to the second leg axis and defined by a curved boundary component in the outer lateral surface, and a substantially straight boundary component in the inner lateral surface, C. a relatively deformable apex member coupling the first proximal end with the second proximal end whereby the first leg axis and the second leg axis are coplanar and extend along a clip axis, whereby the first leg inner lateral surface is opposite the second leg inner lateral surface, wherein the outer lateral surface of the first leg member, and the outer lateral surface of the second leg member, each include a first outer surface lateral boundary and a second outer surface lateral boundary, extending along the respective first leg axis and second leg axis, from the proximal end to the distal end, wherein the inner lateral surface of the first leg member, and the inner lateral surface of the second member, each include: i. an elongated substantially planar central portion extending along the respective first leg axis and second leg axis, from the proximal end to the distal end, and having a first central lateral boundary and a second central lateral boundary, wherein the first lateral boundary and the second lateral boundary extend along the respective first leg axis and second leg axis, from the proximal end to the distal end, ii. first and second elongated clamping portions, wherein each of the first and second elongated clamping portions extends along the respective first leg axis and second leg axis, from the proximal end to the distal end, and includes a first clamp lateral boundary and a second clamp lateral boundary, wherein the first clamp lateral boundary and the second clamp lateral boundary of each clamping portion extends along the respective first leg axis and second leg axis, from the proximal end to the distal end, and wherein each of the first and second elongated clamping portions is S-shaped transverse to the respective first leg axis and second leg axis, and i. defines first and second open-faced concave cross-section grooves extending from the inner lateral surface toward the outer lateral surface, and extending transverse from the first clamp lateral boundaries of the respective first and second clamping portions, and ii. defines first and second convex cross-section ridges extending from the inner lateral surface away from the outer lateral surface, and extending transverse from the second clamp lateral boundaries of the respective first and second clamping portions, wherein the first clamp lateral boundaries of the respective first and second clamping portions are contiguous with the respective first central lateral boundary and second central lateral boundary of the respective central planar portions of the respective first and second leg members, wherein the second clamp lateral boundaries of the respective first and second clamping portions are contiguous with the respective first outer surface lateral boundary and second outer surface lateral boundary of the outer surfaces of the respective first leg member and second leg member, wherein the grooves and ridges of the first leg member are opposite associated grooves and ridges of the second leg member.

In another embodiment of the subject invention, the first leg axis and the second leg axis may be substantially parallel, and substantially parallel to the clip axis.

In a further embodiment of the subject invention, the first leg axis and the second leg axis diverge from the apex member.

In an additional embodiment of the subject invention, the planar central portions of the respective first leg member and second leg member, may include a plurality of open-faced grooves extending transverse to the respective first leg axis and second leg axis.

In a further embodiment of the subject invention, the planar central portions of the respective first leg member and second leg member, may include a textured surface.

In another embodiment of the subject invention, the respective first leg member and second leg member may have a substantially uniform width transverse to the respective first leg axis and second leg axis.

In a further embodiment of the subject invention, the groove concave cross-section may be substantially semi-circular.

In an additional embodiment of the subject invention, the groove concave cross-section may be substantially semi-elliptical.

In another embodiment of the subject invention, the ridge convex cross-section may be substantially semi-circular.

In a further embodiment of the subject invention, the ridge convex cross-section may be substantially semi-elliptical.

Another embodiment of the subject invention, discloses a surgical clip for a clip applier comprising: a first elongated leg member comprising a first proximal end, a first distal end, a first outer surface and a first inner surface, wherein the first outer surface comprises a substantially half-round cross-sectional configuration and the first inner surface comprises a substantial flat first central inner portion such that the first elongated leg member has a substantially D-shaped cross-sectional configuration, wherein the first inner surface further comprises a first elongated concave groove adjacent to a first side of the first central inner portion, a second elongated concave groove adjacent to a second side of the first central inner portion that opposes the first side, a first elongated convex ridge adjacent to the first elongated concave groove, and a second elongated convex ridge adjacent to the second elongated concave groove; a second elongated leg member comprising a second proximal end, a second distal end, a second outer surface and a second inner surface, wherein the second outer surface comprises a substantially half-round cross-sectional configuration and the second inner surface comprises a substantial flat second central inner portion such that the second elongated leg member has a substantially D-shaped cross-sectional configuration, wherein the second inner surface further comprises a third elongated concave groove adjacent to a first side of the second central inner portion, a fourth elongated concave groove adjacent to a second side of the second central inner portion that opposes the first side, a third elongated convex ridge adjacent to the third elongated concave groove, and a fourth elongated convex ridge adjacent to the fourth elongated concave groove; wherein the first proximal end and the second proximal end couple to form a relatively deformable apex for the surgical clip, the first outer surface and the second outer surface form a continuous outer surface, the first central inner portion and the second inner portion form a continuous inner portion, the first elongated concave groove and the third elongated concave groove form a first continuous internal groove, the second elongated concave groove and the fourth elongated concave groove form a second continuous internal groove, the first elongated convex ridge and the third elongated convex ridge form a first continuous internal convex ridge, and the second elongated convex ridge and the fourth elongated convex ridge form a second continuous internal convex ridge.

In another embodiment of the subject invention, the first and second central inner portions, proximate to the first and second distal ends, may each further comprise a plurality of raised surfaces. In another embodiment of the subject invention, the first and second central inner portions may each further comprise a serrated surface. In another embodiment of the subject invention, the first and second central inner portions may each further comprise a textured surface.

In one embodiment of the subject invention, the surgical clip comprises one piece.

In a further embodiment of the subject invention, the surgical clip may be 0.1 to 0.5 inches in length.

In another embodiment of the subject invention, the surgical clip may be composed of titanium or stainless steel. In one embodiment of the subject invention, the surgical clip may be composed of biodegradable material.

In an even further embodiment of the subject invention, there is no minimum vessel closure diameter for the surgical clip.

In another embodiment of the subject invention, the clip may have a substantially U-shaped configuration. In one embodiment of the subject invention, the clip may have a substantially V-shaped configuration.

In another embodiment of the subject invention, the first and second outer surfaces may each have a substantially half-elliptical cross-sectional configuration. In an even further embodiment of the subject invention, the first and second outer surfaces may each have a substantially half-circular cross-sectional configuration.

In a further embodiment of the subject invention, each groove on the inner surface of each leg member may have a substantially half-elliptical cross-sectional configuration. In one embodiment of the subject invention, each groove on the inner surface of each leg member may have a substantially half-circular cross-sectional configuration.

In another embodiment of the subject invention, each ridge on the inner surface of each leg member may have a substantially half-circular cross-sectional configuration. In a further embodiment of the subject invention, each ridge on the inner surface of each leg member may have a substantially half-elliptical uninterrupted cross-sectional configuration.

One embodiment of the subject invention discloses surgical clip for a clip applier comprising first and second leg members connected at their proximal ends and terminating at their distal ends, wherein the distal ends of the first and second leg members are spaced apart and substantially parallel to one another, further wherein the clip comprises a continuous curved outer surface and a continuous tissue gripping surface, wherein the tissue gripping surface comprises a substantial flat inner portion, a set of opposing longitudinal channels separated by the substantially flat inner portion and a set of opposing curved longitudinal ridges on either side of the opposing channels, wherein the proximal ends of the first and second leg members curve towards each other to connect.

In another embodiment of the subject invention, the surgical clip comprises one piece.

In a further embodiment of the subject invention, the surgical clip may be 0.1 to 0.5 inches in length.

In an additional embodiment of the subject invention, the surgical clip may be composed of titanium or stainless steel. In another embodiment of the subject invention, the surgical clip may be composed of biodegradable material.

In one embodiment of the subject invention, there is no minimum vessel closure diameter for the surgical clip.

In a further embodiment of the subject invention, the clip may have a substantially U-shaped configuration. In an additional embodiment of the subject invention, the clip may have a substantially V-shaped configuration.

In one embodiment of the subject invention, the continuous curved outer surface of the clip may have a substantially half-elliptical cross-sectional configuration. In another embodiment of the subject invention, the continuous curved outer surface of the clip may have a substantially half-circular cross-sectional configuration.

In a further embodiment of the subject invention, each continuous groove on the continuous tissue gripping surface of the clip may have a substantially half-elliptical cross-sectional configuration. In an additional embodiment of the subject invention, each continuous groove on the continuous tissue gripping surface of the clip may have a substantially half-circular cross-sectional configuration.

In one embodiment of the subject invention, each continuous ridge on the continuous tissue gripping surface of the clip may have a substantially half-circular uninterrupted cross-sectional configuration. In another embodiment of the subject invention, each continuous ridge on the continuous tissue gripping surface the clip may have a substantially half-elliptical uninterrupted cross-sectional configuration.

One embodiment of the subject invention discloses a method of securely ligating a vessel, comprising the steps of: a) providing a surgical clip with first and second leg members connected at their proximal ends and terminating at their distal ends, wherein the distal ends of the first and second leg members are spaced apart and substantially parallel to one another, further wherein each leg member comprises a curved outer surface and an inner surface, wherein each inner surface comprises a substantial flat inner portion, a set of opposing grooves separated by the substantially flat inner portion and a set of opposing curved ridges on either side of the opposing grooves, wherein the proximal ends of the first and second leg members curve towards each other to connect such that the surgical clip comprises a continuous curved outer surface from the curved outer surfaces of each leg member and a continuous inner surface from the inner surfaces of each leg member including a continuous substantially flat inner portion, a continuous set of opposing grooves separated by the continuous substantially flat inner portion, and a continuous set of opposing curved ridges; b) placing the vessel between the inner surfaces of said first and second leg members; c) applying equal compressive forces against said first and second leg members in opposing directions so as to clamp the vessel between the inner surfaces of the first and second leg members, wherein the surgical clip bends at the connection of proximal ends of the first and second leg members, and further wherein each of the opposing grooves and opposing ridges on the inner surface of the first leg align with the opposing grooves and opposing ridges on the inner surface of the second leg when the surgical clip is compressed; and d) removing the compressive forces from the clip, wherein the connection of proximal ends of the first and second leg member remains in a bent, compressed position to maintain ligation of the vessel.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which:

FIG. 14 illustrates a perspective view of the distal end of a surgical clip applier apparatus along line C-C of FIG. 13.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

The subject invention comprises a surgical vessel ligating clip 1, as shown in FIGS. 1-14.

Figure 8:
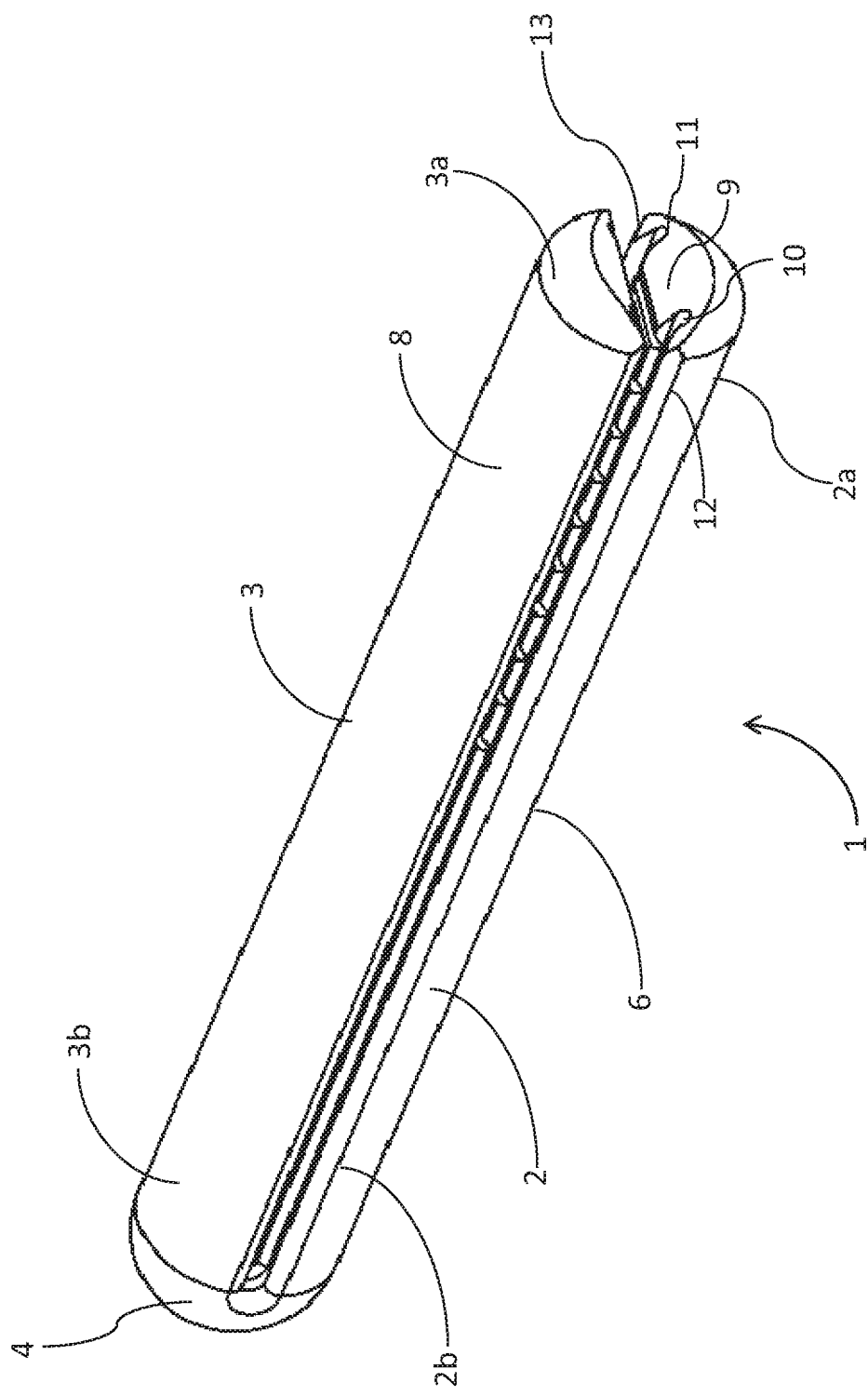
FIG. 8 illustrates a perspective view of the surgical vessel ligating clip in the compressed or closed position.
Figure 9:
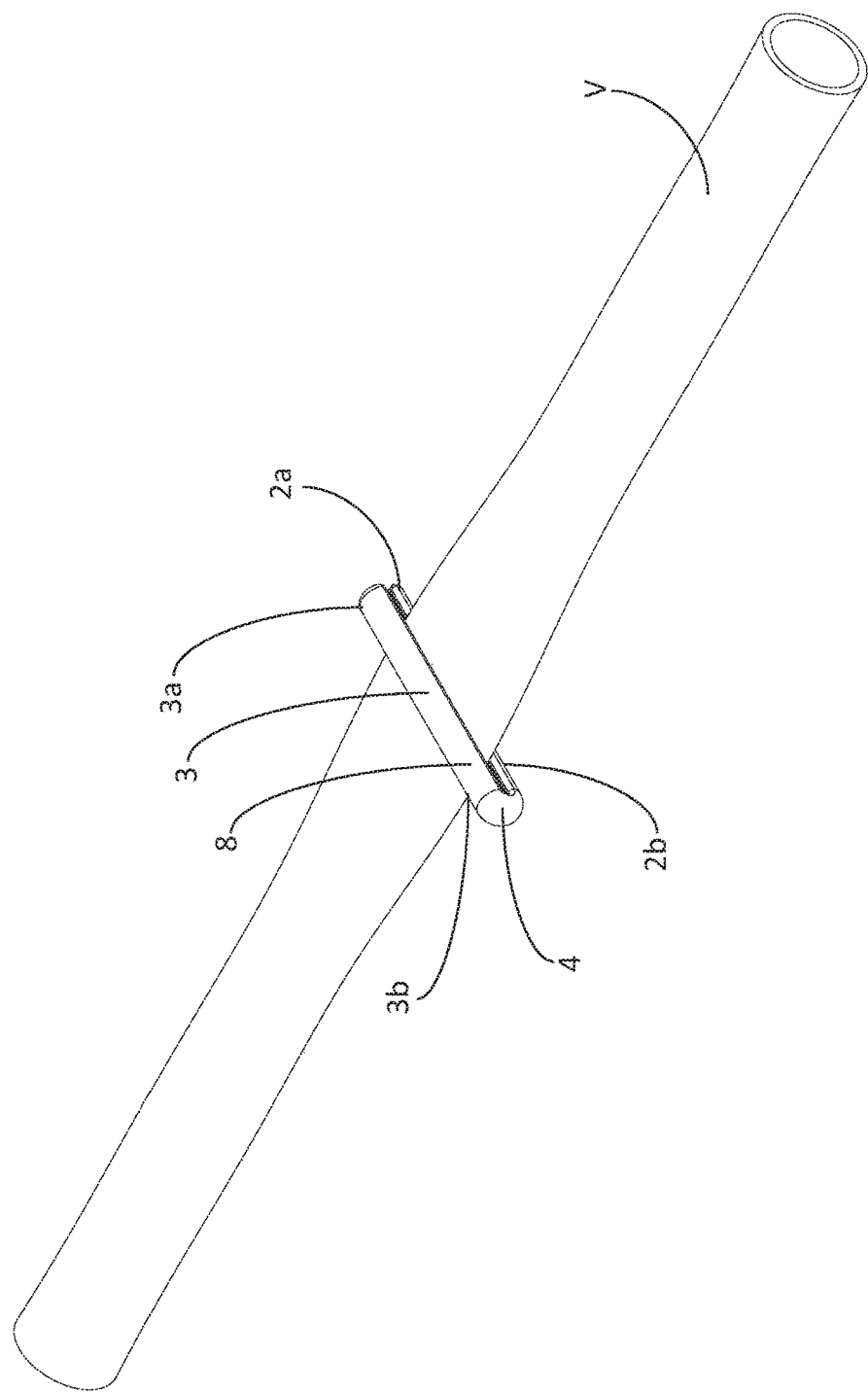
FIG. 9 illustrates a perspective view of the surgical vessel ligating clip in the compressed or closed position applied to a tubular vessel.
Figure 10:
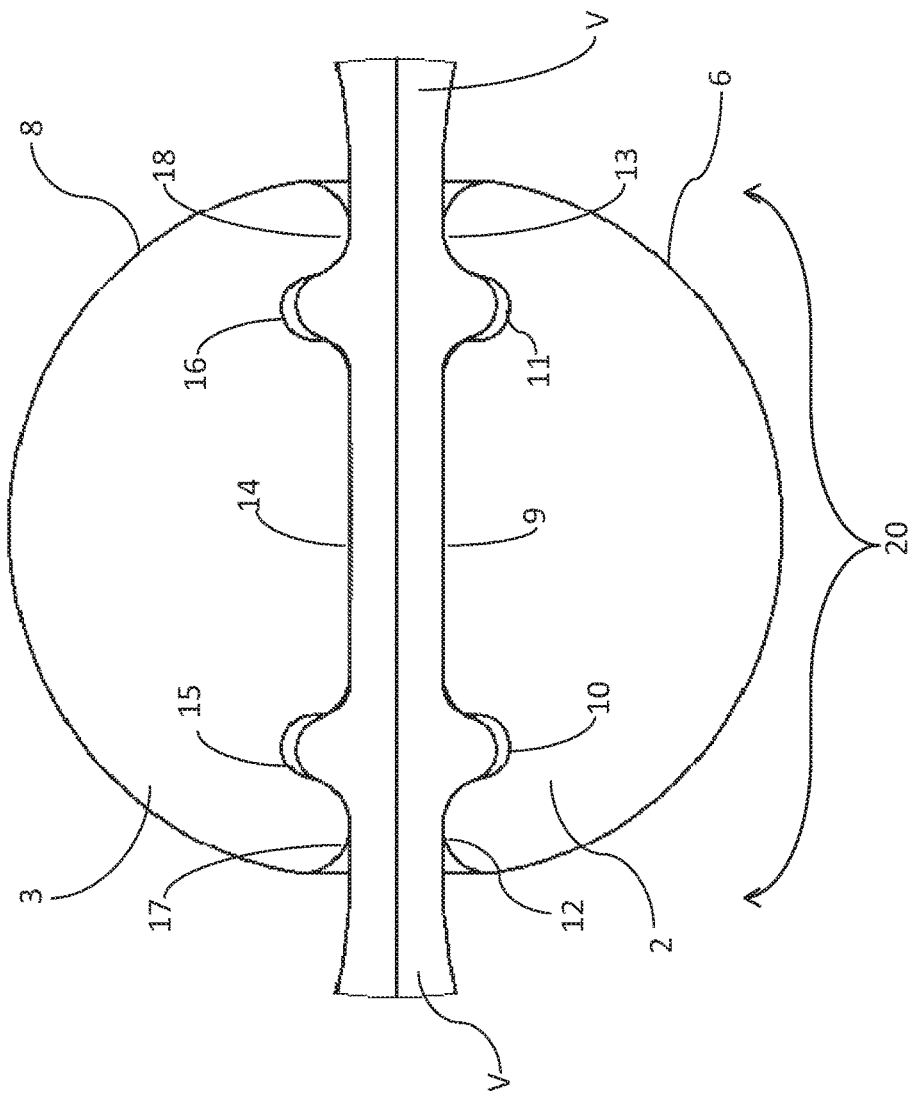
FIG. 10 illustrates an enlarged front cross sectional view of the surgical vessel ligating clip in the compressed or closed position applied to a tubular vessel.

FIGS. 1, 3, 5 and 6 illustrate the surgical vessel ligating clip 1 in the open or uncompressed position. The surgical vessel ligating clip 1 will be in an open position before attachment or application over a blood vessel to ligate or occlude that vessel. FIGS. 8-10 illustrate the closed or compressed position of surgical vessel ligating clip 1 alone and clamped over a tubular vessel V.

Figure 1:
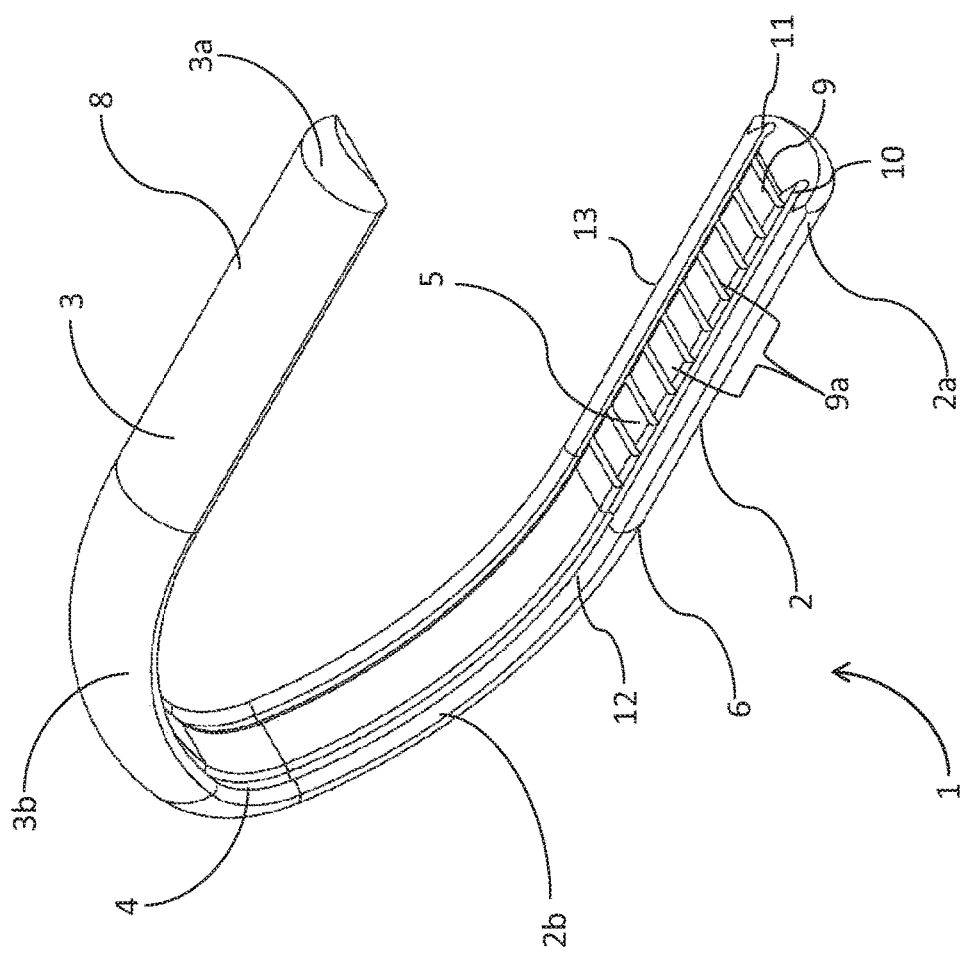
FIG. 1 illustrates a perspective view of the surgical vessel ligating clip in the open position.
Figure 2:
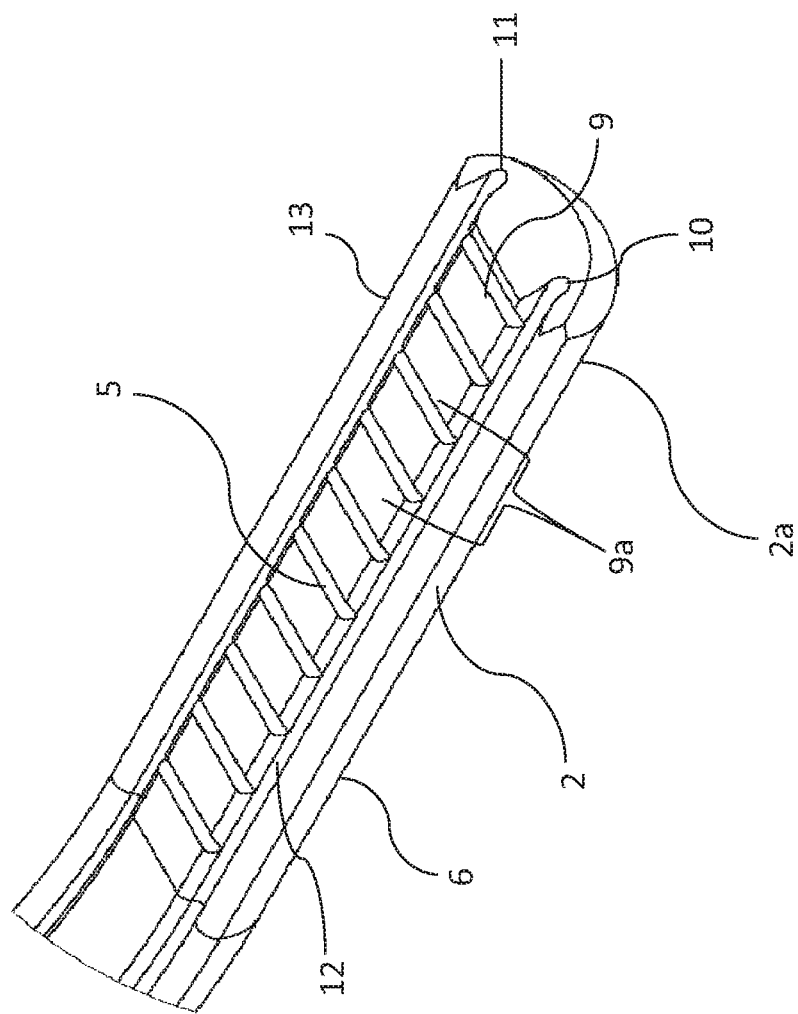
FIG. 2 illustrates an enlarged perspective view of one ligating leg of the surgical vessel ligating clip.
Figure 3:
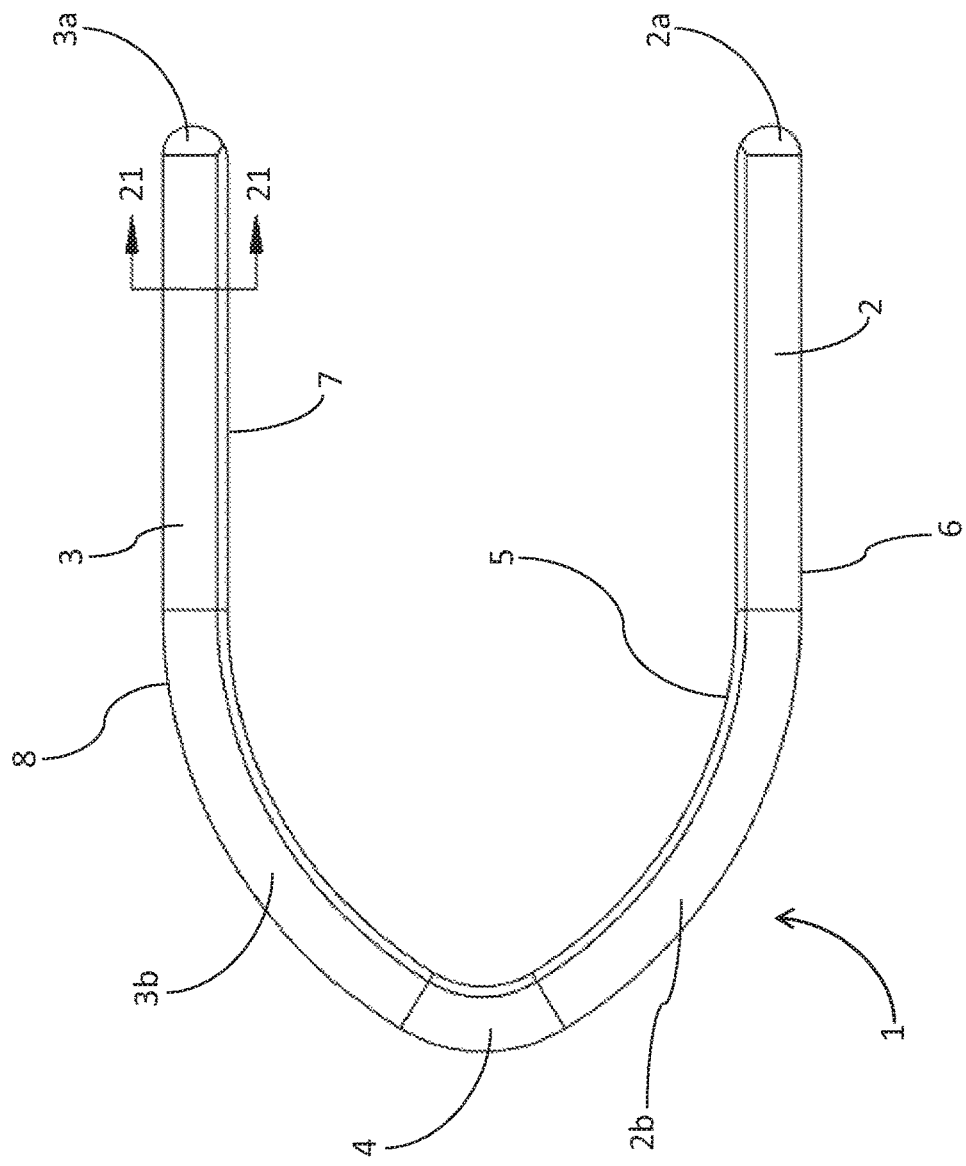
FIG. 3 illustrates a side elevational view of the surgical vessel ligating clip in the open position.

Surgical vessel ligating clip 1 has a generally U-shaped configuration as shown in FIGS. 1 and 3. In other embodiments of the subject invention, surgical vessel ligating clip 1 may have a V-shaped configuration, another symmetrical. configuration, or even an asymmetrical configuration.

The surgical vessel ligating clip 1 includes a pair of opposed elongated ligating legs 2 and 3, each having respective distal ends 2a and 3a, and respective proximal ends 2b and 3b. Ligating legs 2 and 3 have substantially uniform widths and lengths. Ligating legs 2 and 3 are substantially mirror images of each other. The distal ends 2a and 3a of ligating legs 2 and 3 are substantially parallel to one another and are relatively non-deformable.

The proximal ends 2b and 3b of the ligating legs 2 and 3 curve towards each other to form apex connection 4. Apex connection 4 is relatively deformable to allow the surgical vessel ligating clip 1 to compress from the open position to the closed position illustrated in FIGS. 8-10.

Ligating leg 2 contains an inner tissue contacting surface 5 and an outer surface 6 that both extend along the axis of ligating leg 2 in a substantially parallel direction. Ligating leg 3 contains an inner tissue contacting surface 7 and an outer surface 8 that both extend along the axis of ligating leg 3 in a substantially parallel direction.

Figure 4:
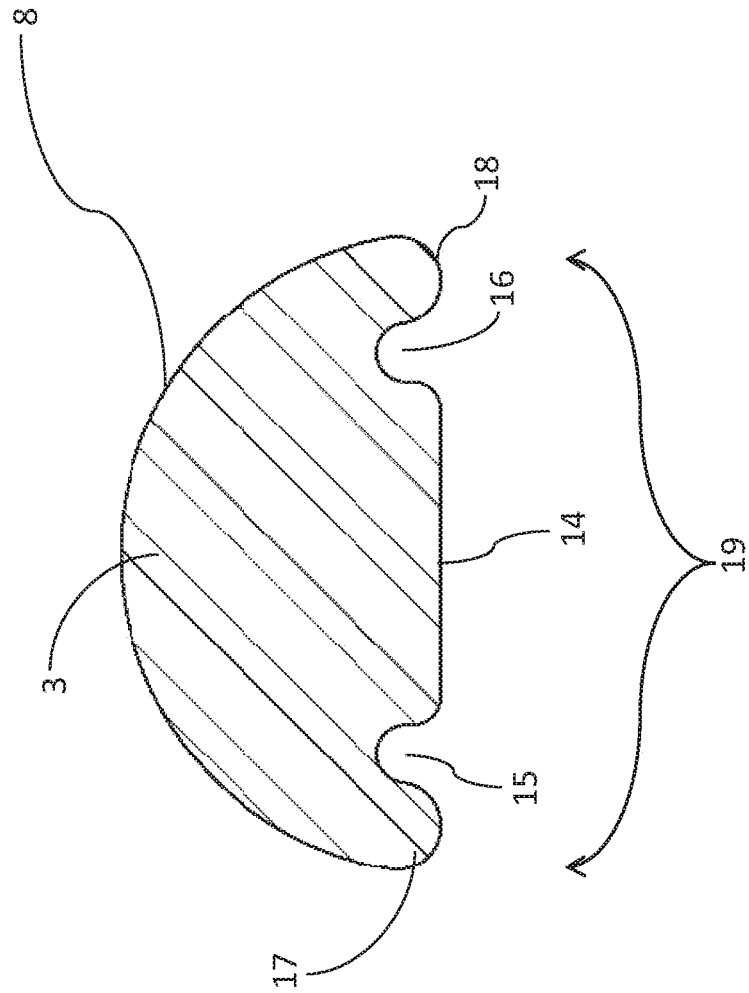
FIG. 4 illustrates an enlarged cross sectional view of the surgical vessel ligating clip along line 21-21 of FIG. 2.
Figure 5:
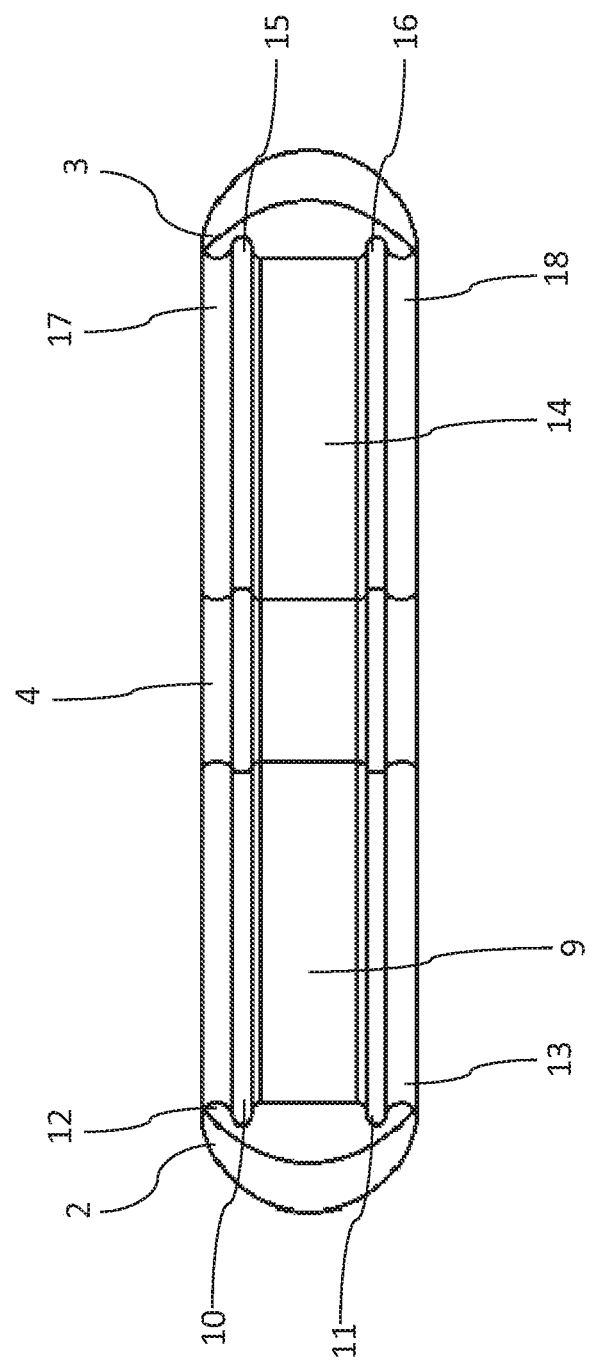
FIG. 5 illustrates a front view of the surgical vessel ligating clip in the open position.
Figure 6:
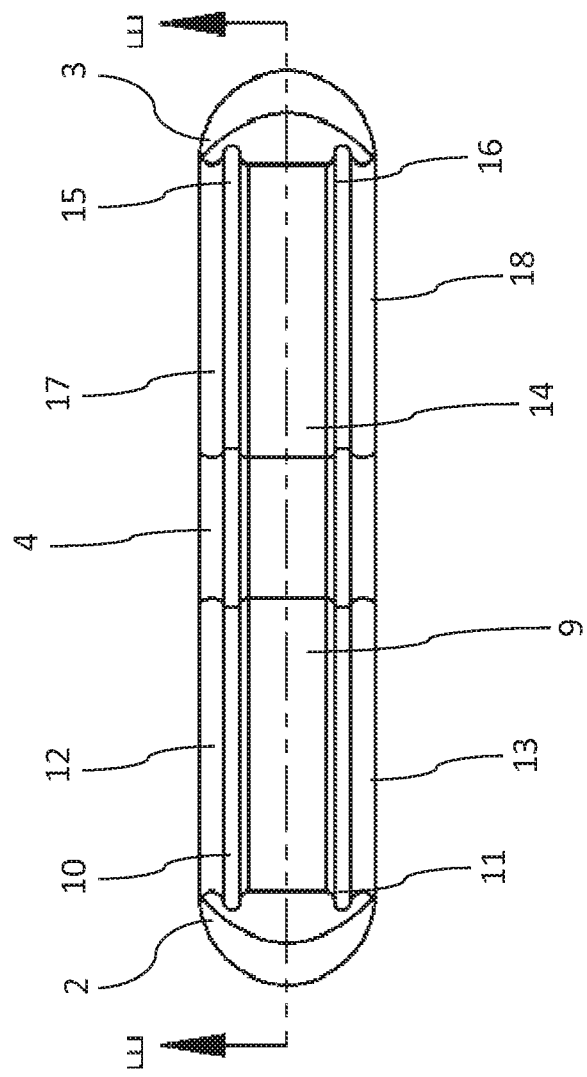
FIG. 6 illustrates another front view of the surgical vessel ligating clip in the open position.
Figure 7:
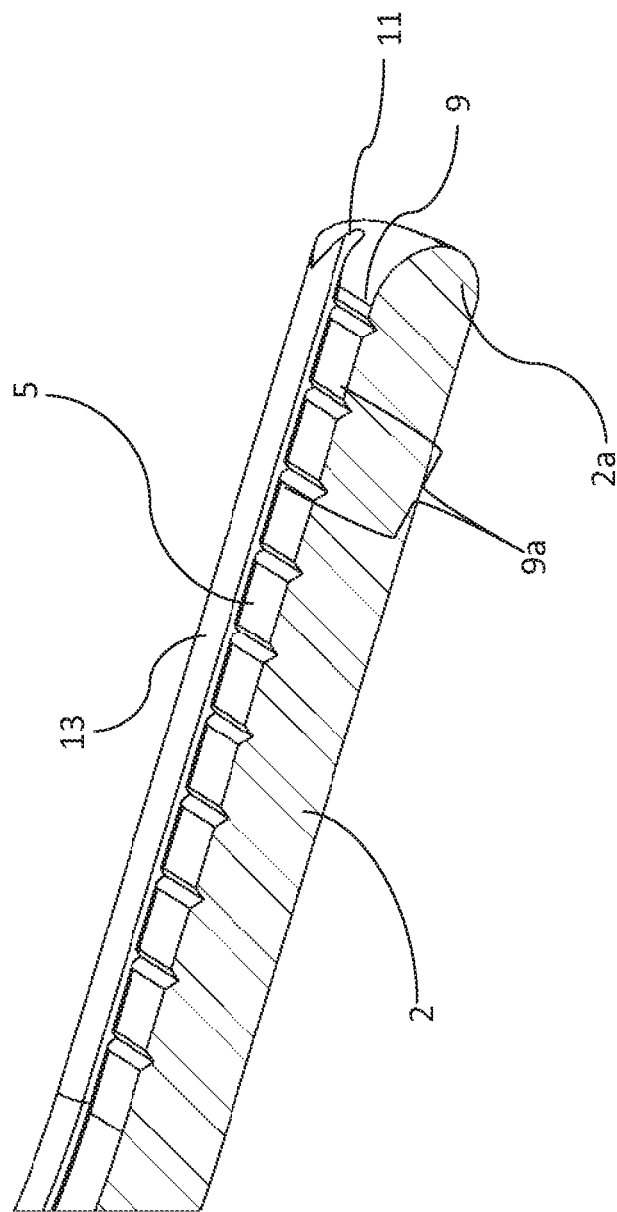
FIG. 7 illustrates an enlarged perspective view of one ligating leg of the surgical vessel ligating clip along line E-E of FIG. 6.

Outer surfaces 6 and 8 each have a substantially half-round cross-sectional configuration. In other embodiments of the subject invention, the outer surfaces of each ligating leg may each have a substantially half-elliptical cross-sectional configuration. FIGS. 4 and 10 illustrate enlarged cross-sectional views of ligating legs 2 and 3. Inner tissue contacting surface 5 and outer surface 6 form a substantially D-shaped cross-sectional configuration for ligating leg 2. Inner tissue contacting surface 7 and outer surface 8 form a substantially D-shaped cross-sectional configuration for ligating leg 3. Ligating legs 2 and 3 are substantially equivalent in size and shape.

As illustrated in FIGS. 1, 2, 5, 10 and 12, inner tissue contacting surface 5 of ligating leg 2 contains a substantially flat inner central surface 9 with opposing, open-faced, concave grooves 10 and 11 on either side. Inner tissue contacting surface 5 further contains two opposing convex ridges 12 and 13 on the outer sides of opposing grooves 10 and 11, respectively.

As illustrated in FIGS. 4, 5, 10 and 12, inner tissue contacting surface 7 of ligating leg 3 contains a substantially flat inner central 14 with opposing, open-faced, concave grooves 15 and 16 on either side. Inner tissue contacting surface 7 further contains two opposing convex ridges 17 and 18 on the outer sides of opposing grooves 15 and 16, respectively.

Grooves 10 and 11 each have a substantially half-round cross-sectional configuration with respect to inner tissue contacting surface 5 on ligating leg 2. Grooves 15 and 16 each have a substantially half-round cross-sectional configuration with respect to inner tissue contacting surface 7 on ligating leg 3. In other embodiments of the subject invention, grooves 10, 11, 15 and 16 may each have a substantially half-elliptical cross-sectional configuration. As illustrated in FIG. 10, these rounded configurations of grooves 10, 11, 15 and 16 prevent cutting or piercing of ligated vessel tissue.

Ridges 12 and 13 each have a substantially half-round cross-sectional configuration with respect to inner tissue contacting surface 5 on ligating leg 2. Ridges 17 and 18 each have a substantially half-round cross-sectional configuration with respect to inner tissue contacting surface 7 on ligating leg 3. In other embodiments of the subject invention, ridges 12, 13, 17 and 18 may each have a substantially half-elliptical cross-sectional configuration. As illustrated in FIG. 10, these rounded configurations of ridges 12, 13, 17 and 18 prevent cutting or piercing of ligated vessel tissue.

Grooves 10 and 11 and ridges 12 and 13 are all continuous from distal end 2a to proximal end 2b and extend along ligating leg 2 in a substantially parallel direction. Grooves 15 and 16 and ridges 17 and 18 are all continuous from distal end 3a to proximal end 3b and extend along ligating leg 3 in a substantially parallel direction. As ligating legs 2 and 3 curve towards each another to their respective proximal ends, 2b and 3b, to be connected at apex connection 4; grooves 10 and 15, grooves 11 and 16, ridges 12 and 17, and ridges 13 and 18 all meet to form uninterrupted, continuous structures on clip 1. Accordingly, the inner tissue contacting surfaces 5 and 7, and the outer surfaces 6 and 8 are both uninterrupted, continuous structures on surgical clip 1 as ligating legs 2 and 3 curve towards each another to connect at apex connection 4. Thus, surgical clip 1 contains an uninterrupted, continuous outer surface with a substantially half-round cross-sectional configuration and an uninterrupted, continuous internal surface with a substantially flat inner central surface with opposing, open-faced, concave grooves on either side, and further contains two opposing convex ridges on either side of the opposing grooves.

Substantially flat inner central surfaces 9 and 14 may further contain pluralities of serrated teeth. These pluralities of serrated teeth are substantially perpendicular with respect to inner tissue contacting surfaces 5 and 7. The plurality of serrated teeth 9a extends from distal end 2a along ligating leg 2 in a substantially parallel direction, to end proximate to the point at which ligating leg 2 begins to curve towards ligating leg 3. The plurality of serrated teeth ligating leg 3 (not shown) extends from distal end 3a along ligating leg 3 in a substantially parallel direction, to end proximate to the point at which ligating leg 3 begins to curve towards ligating leg 2.

FIGS. 4 and 10 illustrate the double S-shaped cross-sectional configuration 19 of ligating leg 3 of the surgical vessel ligating clip 1. Double S-shaped cross-sectional configuration 19 is formed from the S-shaped cross-sectional configuration of groove 15 and ridge 17, and the S-shaped cross-sectional configuration of groove 16 and ridge 18. FIGS. 1, 2, 5 and 10 illustrate the double S-shaped cross-sectional configuration 20 of ligating leg 2 that opposes and is a mirror image of configuration 19 on ligating leg 3. Double S-shaped cross-sectional configuration 20 is formed from the S-shaped cross-sectional configuration of groove 10 and ridge 12, and the S-shaped cross-sectional configuration of groove 11 and ridge 13. Double S-shaped cross-sectional configurations 19 and 20 allow surgical clip 1 to be securely ligated to a vessel.

FIG. 8 illustrates an isometric view of the surgical vessel ligating clip 1 in the closed or compressed position (vessel V not shown). FIG. 9 illustrates the closed position of surgical vessel ligating clip 1 attached to vessel V.

FIG. 10 illustrates an enlarged cross-sectional view of the surgical vessel ligating clip 1 in the compressed or closed position applied to a tubular vessel V. Ligating leg 3 is compressed over ligating leg 2. The grooves of both legs 2 and 3 form substantially elliptical cross-sectional spaces, with groove 15 of leg 3 being disposed over groove 10 of leg 2; and groove 16 of leg 3 being disposed over groove 11 of leg 2. The vessel, as illustrated by reference letter V, traverses through ridges 17 and 12; into grooves 15 and 10; through substantially flat central surfaces 14 and 9; through the grooves 16 and 11; and finally through ridges 18 and 13. No internal fluid traverses vessel V when clip 1 is compressed over the vessel The structures of inner tissue contacting surfaces 5 and 7 promote ligation or occlusion of a tubular blood vessel without piercing or cutting the vessel. Once the surgical clip 1 is closed or compressed over a tubular vessel, the vessel tissue may gradually move or ooze into the spaces between grooves 10, 11, 15 and 16 while remaining frictionally engaged by the compressive force applied by substantially flat central surfaces 9 and 14 and ridges 12, 13, 17 and 18; such that the clip 1 does not move or become loose on the vessel. The half rounded edges of grooves 10, 11, 15 and 16, and ridges 12, 13, 17 and 18, do not pierce or cut the vessel during ligation. The substantially half-round cross-sectional configuration of outer surfaces 6 and 8 do not pierce or cut surrounding tissue.

Figure 13:
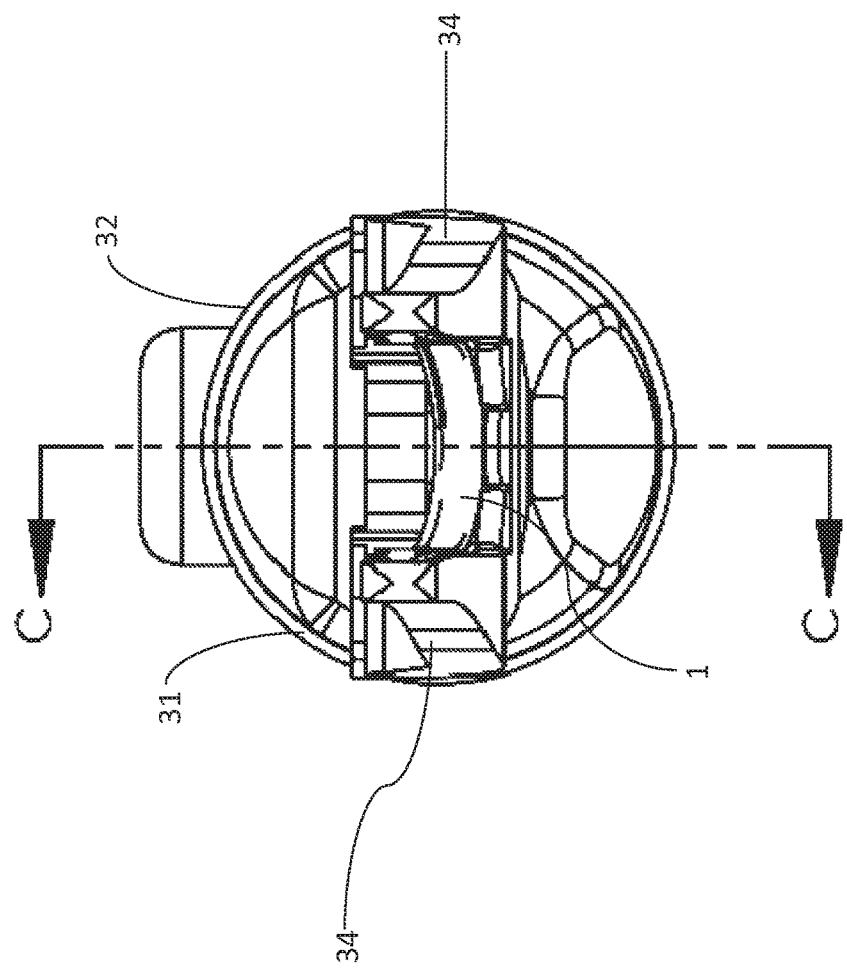
FIG. 13 illustrates a front view of the distal end of a surgical clip applier apparatus containing a surgical vessel ligating clip.

The surgical clip 1 of the subject invention is applied to body tissue by the distal end 31 of surgical clip applier apparatus 32. FIG. 13 illustrates a front view of the distal end 31 of a surgical clip applier apparatus 32 containing a surgical vessel ligating clip 1. FIG. 14 illustrates a perspective view of the distal end 31 of a surgical clip applier apparatus 32 along line C-C of FIG. 13. A surgical clip applying apparatus 32 generally has a long, narrow structure 33 that contains a plurality of internal clips 1 in sequence and positions a clip 1 proximate to the target vessel.

The end of this long narrow structure 33 has a mechanism, such as a jaws assembly 34. The surgical vessel ligating clip 1 is maintained in the open position in jaws assembly 34 of a surgical clip applying apparatus 32 by applying two initial compressive forces in opposing directions to the outer surface of each leg 2 and 3 until the desired tissue is reached through a small incision in the patient. Inner tissue contacting surface 5 of leg 2 is placed on one side of a vessel V to be ligated and inner tissue contacting surface 7 of leg 3 is placed on the opposing side of vessel V. The jaws assembly 34 increases the two equal compressive forces in opposing directions to the outer surface of each leg 2 and 3 towards the center of the surgical clip 1. As jaws assembly 34 increases the two equal compressive forces to the outer surface of each leg 2 and 3, the legs to bend at the apex connection 4 and the distance between inner tissue contacting surface 5 and inner tissue contacting surface 7 is reduced as the distal ends 2a and 3a are brought closer to each other. As this distance is reduced, ridges 12 and 17, ridges 13 and 18 and substantially flat inner surfaces 9 and 14 attach to opposing sides of the vessel V, respectively. As this distance is further reduced, the vessel V diameter is reduced to a desired level.

Once the surgical clip 1 is closed, the distal ends 2a and 3a of ligating legs 2 and 3 will remain substantially parallel to one another. The vessel V will be closed by the opposing inner tissue contacting surface 5 and the inner tissue contacting surface 7. Apex 4 retains the closed position of the surgical clip 1 assuring that the vessel V remains ligated. The continuous outer surface of surgical clip 1 with a substantially half-round cross-sectional configuration will reduce irritation and trauma in tissue surrounding the ligated vessel, since it does not have any sharp corners or edges that may pierce or cut surrounding tissue.

The pluralities of teeth 9a on the substantially flat surfaces 9 and 14, provide additional friction on slippery blood vessels to prevent the clip from moving or slipping from the vessel.

Figure 11:
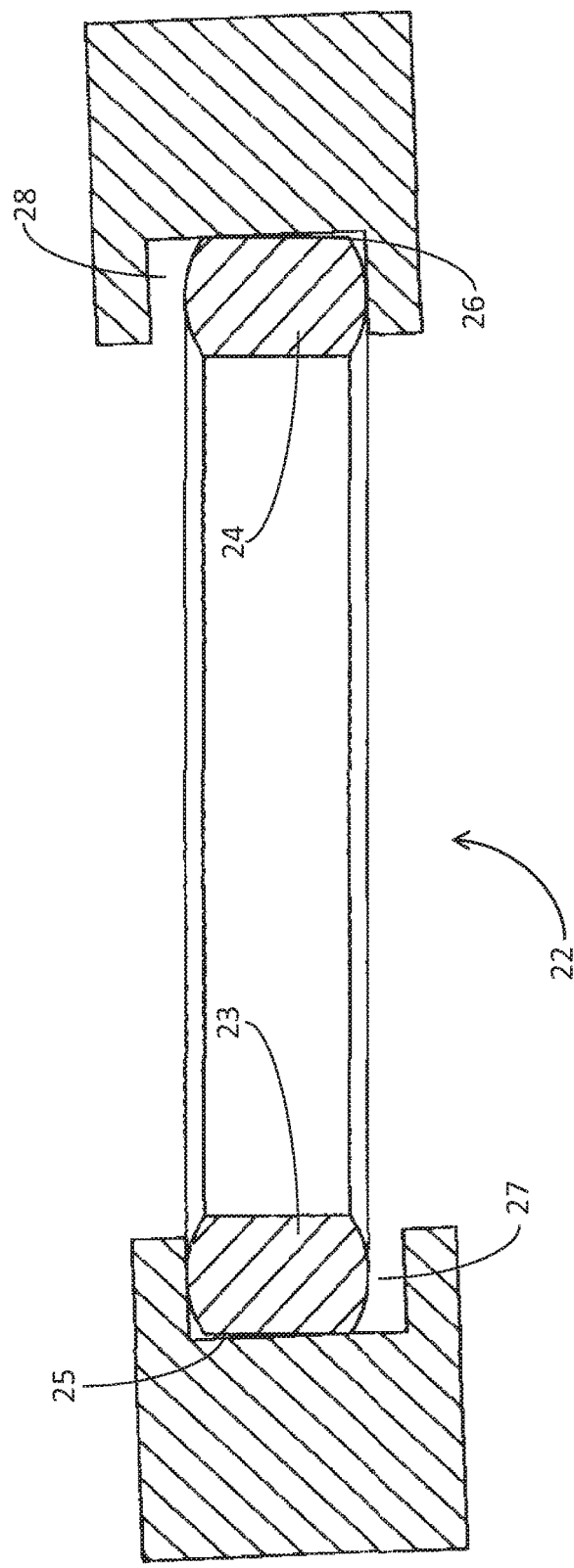
FIG. 11 illustrates a front elevational view of a surgical clip of the prior art in the internal grooves of a surgical clip applier apparatus illustrating the non-parallel ligating position of the clip legs that results in the scissoring effect.

Surgical clips of the prior art deform in shape when applied by a surgical clip applying apparatus. As illustrated in FIG. 11, surgical clips 22 of the prior art have legs 23 and 24 with straight-edged outer surfaces 25 and 26. These prior art clips 22 are inserted into the internal grooves 27 and 28 of a jaws assembly 34. The internal grooves 27 and 28 of jaws assembly 34 must be large enough to allow clip 22 to have clearance on both sides to pass through onto the vessel, however, jaws assembly 34 must also initially apply two equal compressive forces in opposing directions to the outer surface of each leg of clip 22. These initial compressive forces are required to hold the clip 22 in place for ligation. Once the surgical clip applying apparatus reaches the target vessel, jaws assembly 34 will deform the clip 22 by increasing these two equal compressive forces in opposing directions to the outer surface of each leg towards the center of the surgical clip.

The grooves 27 and 28 of the surgical clip applying apparatus and the legs 23 and 24 of clip 22 have different tolerances for compressive forces. Once the jaws assembly 34 initially applies compressive forces to clip 22 to hold it in place for ligation, the different tolerances for these initial compressive forces cause the legs 23 and 24 of clip 22 to move to opposing corners of internal grooves 27 and 28 through the clearance space on both sides. This movement causes the legs 23 and 24 to be held in a non-parallel position within the jaws assembly 34.

As the jaws assembly 34 ligates clip 22 over a vessel, it increases these two equal compressive forces in opposing directions to the outer surface of each leg 23 and 24. Since these legs 23 and 24 are held in a non-parallel position, these increased compressive forces are not applied evenly to legs 23 and 24. This unevenly applied compressive force results in displacement of each end of legs 23 and 24 over the vessel. This displacement is called the scissoring effect because it results in the piercing or cutting of vessels. Scissoring can also prevent the clip from closing completely about the vessel.

The outer surfaces 6 and 8 of ligating legs 2 and 3 of surgical clip 1 allows for full control of both legs 2 and 3 of the clip 1 by the jaw assembly 34 and thus eliminates the possibility of scissoring.

Figure 12:
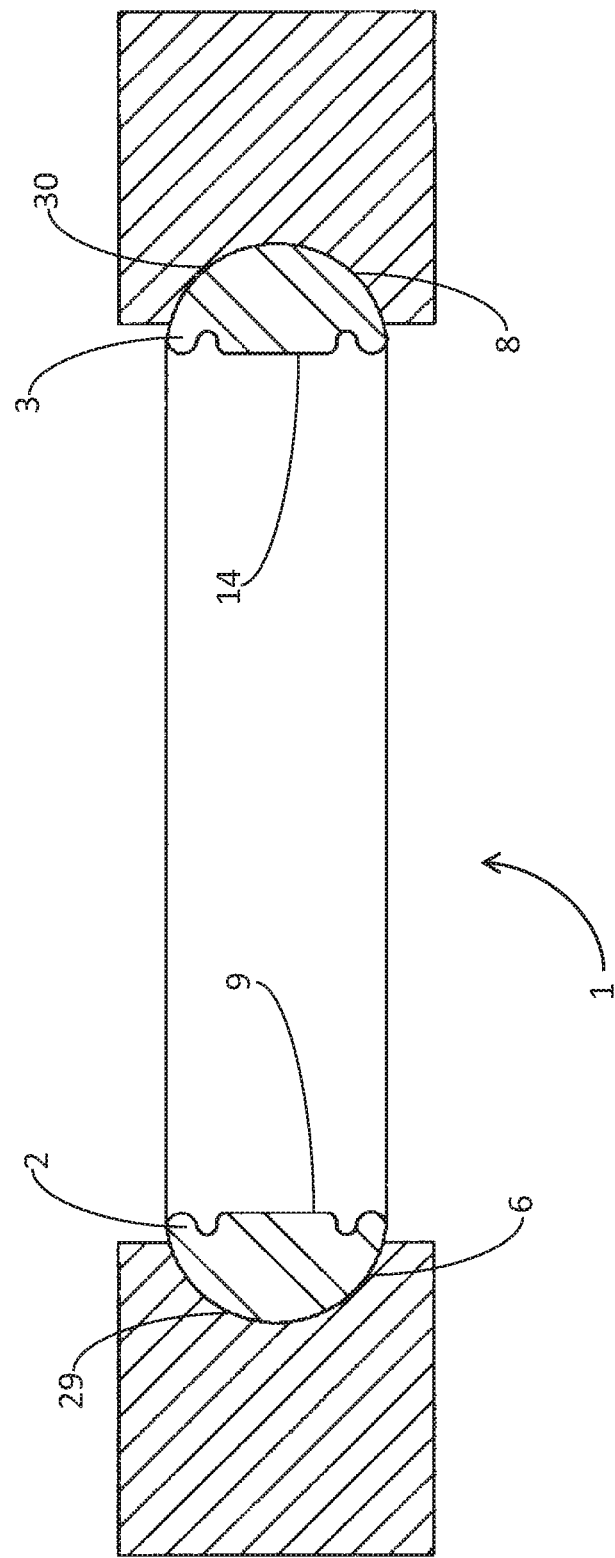
FIG. 12 illustrates a front elevational view of the surgical vessel ligating clip with outer surface configurations that complement the internal grooves of a surgical clip applier apparatus to control for parallelism in the ligating position of the clip legs that results in prevention of clip scissoring.

As shown in FIG. 12, surgical clip 1 has legs 2 and 3 with outer surfaces 6 and 8 that have substantially half-round cross-sectional configurations. Clip 1 is inserted into internal, open-faced, concave grooves 29 and 30 of a jaws assembly 34. These grooves 29 and 30 also have substantially half-round cross-sectional configurations. Due to the complementary configurations of outer surface 6 to internal groove 29 and outer surface 8 to internal groove 30, the surgical clip 1 has enough space to pass through jaws assembly 34. However, grooves 29 and 30 do not permit legs 2 and 3 to move away from a substantially parallel position. Once the jaws assembly 34 initially applies compressive forces to clip 1 to hold it in place for ligation, grooves 29 and 30 do not permit legs 2 and 3 to move away from a substantially parallel position.

Thus, as the jaws assembly 34 ligates clip 1 over a vessel, the increased compressive forces are applied evenly to the outer surfaces of legs 2 and 3. This evenly applied compressive force prevents any displacement or scissoring of clip 1 over the vessel.

In one embodiment of the subject invention, the surgical clip 1 is 0.1 to 0.5 inches in length or width. In another embodiment of the subject invention, surgical clip is 0.25 inches in length. In a further embodiment of the subject invention, the surgical clip 1 is intended to be used with a five millimeter trocar. In one embodiment of the subject invention, the internal angle of the apex connection 4 is from 110 degrees to 150 degrees. In a further embodiment of the subject invention, the surgical clip is composed of titanium, stainless steel, tantalum, plastics materials, or a combination thereof. In an even further embodiment of the subject invention, the surgical clip is composed of biodegradable material.

The surgical clips of the subject invention may have up to a 20% greater occlusion area than other surgical clips within a five-millimeter trocar.

In another embodiment of the subject invention, there is no minimum vessel closure diameter for the surgical clip.

What is claimed is:

1. A surgical clip, comprising:
a first elongate member having a distal end portion and a proximal end portion, the first elongate member having an inner surface extending along the distal end portion and the proximal end portion of the first elongate member and an outer surface collectively forming a first rounded edge and a second rounded edge substantially parallel to the first rounded edge, each of the first rounded edge and the second rounded edge extending between the proximal end portion and the distal end portion of the first elongate member, the inner surface defining a first recess disposed between the first rounded edge and a central portion of the inner surface and a second recess defined between the second rounded edge and the central portion, the central portion defining a plurality of grooves extending between and perpendicular to the first recess and the second recess; and a second elongate member having a distal end portion and a proximal end portion, the proximal end portion of the second elongate member being coupled to the proximal end portion of the first elongate member, the second elongate member having an inner surface extending along the distal end portion and the proximal end portion of the second elongate member and an outer surface collectively forming a third rounded edge and a fourth rounded edge substantially parallel to the third rounded edge, each of the third rounded edge and the fourth rounded edge extending between the proximal end portion and the distal end portion of the second elongate member, the inner surface of the second elongate member defining a third recess disposed between the third rounded edge and a central portion of the inner surface of the second elongate member and a fourth recess defined between the fourth rounded edge and the central portion of the inner surface of the second elongate member, the central portion of the second elongate member defining a plurality of grooves extending between and perpendicular to the third recess and the fourth recess;

wherein:
the plurality of grooves of the central portion of the first elongate member form a plurality of teeth between the first recess and the second recess extending only along the central portion of the distal end portion of the first elongate member and not along the central portion of the proximal end portion of the first elongate member, the plurality of grooves of the central portion of the second elongate member form a plurality of teeth between the third recess and the fourth recess extending only along the central portion of the distal end portion of the second elongate member and not along the central portion of the proximal end portion of the second elongate member the first rounded edge and the third rounded edge collectively form a first continuous rounded edge between the distal end portion of the first elongate member and the distal end portion the second elongate member, the second rounded edge and the fourth rounded edge collectively form a second continuous rounded edge between the distal end portion of the first elongate member and the distal end portion of the second elongate member the first recess and the third recess collectively form a first continuous recess between the distal end portion of the first elongate member and the distal end portion of the second elongate member, the first continuous recess is adjacent to the first continuous rounded edge, and the second recess and the fourth recess collectively form a second continuous recess between the distal end portion of the first elongate member and the distal end portion of the second elongate member, the second continuous recess is adjacent to the second continuous rounded edge.

2. The surgical clip of claim 1, wherein the first rounded edge and the first recess collectively form an S-shaped cross-sectional shape.

3. The surgical clip of claim 1, wherein the surgical clip is configured to be transitioned from an open configuration to a closed configuration,
the first rounded edge and the second rounded edge being aligned with the third rounded edge and the fourth rounded edge, respectively, when the surgical clip is in the closed configuration, and the first recess and the second recess being aligned with the third recess and the fourth recess, respectively, when the surgical clip is in the closed configuration.

* * * * *